US010258228B2

(12) United States Patent
Genovese et al.

(10) Patent No.: US 10,258,228 B2
(45) Date of Patent: Apr. 16, 2019

(54) RETRACTION DEVICES, SYSTEMS, AND METHODS FOR MINIMALLY INVASIVE SPINAL SURGERY

(71) Applicant: K2M, Inc., Leesburg, VA (US)

(72) Inventors: Daniel Genovese, Arlington, VA (US); Collin Young, Charlottesville, VA (US)

(73) Assignee: K2M, Inc., Leesburg, VA (US)

( * ) Notice: Subject to any disclaimer, the term of this patent is extended or adjusted under 35 U.S.C. 154(b) by 635 days.

(21) Appl. No.: 14/822,188

(22) Filed: Aug. 10, 2015

(65) Prior Publication Data

US 2016/0038195 A1 Feb. 11, 2016

Related U.S. Application Data

(60) Provisional application No. 62/035,017, filed on Aug. 8, 2014.

(51) Int. Cl.
*A61B 1/32* (2006.01)
*A61B 17/02* (2006.01)
*A61B 17/70* (2006.01)
*A61B 17/16* (2006.01)

(52) U.S. Cl.
CPC ............ *A61B 1/32* (2013.01); *A61B 17/0206* (2013.01); *A61B 17/0218* (2013.01); *A61B 17/1671* (2013.01); *A61B 17/7082* (2013.01)

(58) Field of Classification Search
CPC ....... A61B 1/32; A61B 17/02; A61B 17/0206; A61B 17/0218; A61B 17/16; A61B 17/1602; A61B 17/1604; A61B 17/1613; A61B 17/1615; A61B 17/1617; A61B 17/162; A61B 17/7082

USPC ...................................................... 606/79, 80
See application file for complete search history.

(56) References Cited

U.S. PATENT DOCUMENTS

| | | | |
|---|---|---|---|
| 4,545,374 A * | 10/1985 | Jacobson | A61B 17/0218 600/210 |
| 4,862,891 A | 9/1989 | Smith | |
| 5,171,279 A * | 12/1992 | Mathews | A61B 17/70 128/898 |
| 5,295,994 A | 3/1994 | Bonutti | |
| 5,472,426 A * | 12/1995 | Bonati | A61B 17/1604 600/564 |
| 5,487,739 A | 1/1996 | Aebischer et al. | |
| 5,741,261 A | 4/1998 | Moskovitz et al. | |
| 5,792,044 A | 8/1998 | Foley et al. | |
| 6,152,871 A | 11/2000 | Foley et al. | |
| 6,159,179 A * | 12/2000 | Simonson | A61B 17/0218 604/117 |
| 6,206,826 B1 * | 3/2001 | Mathews | A61B 17/025 600/210 |

(Continued)

*Primary Examiner* — Eric S Gibson
(74) *Attorney, Agent, or Firm* — Lerner, David, Littenberg, Krumholz & Mentlik, LLP

(57) ABSTRACT

A system for mounting a retractor tube to a spine without a guidewire is disclosed. The system includes an awl, a first dilator configured to be advanced over the awl, a retractor tube configured to be advanced over the first dilator, wherein an outer surface of the retractor tube defines a plurality of channels, and a plurality of pins adapted to be received within the plurality of channels, wherein the plurality of pins secure the retractor tube to the at least one vertebral body of the spine. A method for selectively mounting a retractor tube to a spine without a guidewire is also disclosed.

13 Claims, 22 Drawing Sheets

(56) References Cited

U.S. PATENT DOCUMENTS

| | | | |
|---|---|---|---|
| 6,264,651 B1 | 7/2001 | Underwood et al. | |
| 6,360,750 B1 * | 3/2002 | Gerber | A61N 1/0551 |
| | | | 128/898 |
| 6,371,968 B1 * | 4/2002 | Kogasaka | A61B 17/00234 |
| | | | 600/201 |
| 6,851,430 B2 | 2/2005 | Tsou | |
| 6,916,330 B2 * | 7/2005 | Simonson | A61B 17/025 |
| | | | 606/191 |
| 6,945,933 B2 | 9/2005 | Branch et al. | |
| 7,008,431 B2 * | 3/2006 | Simonson | A61B 17/0218 |
| | | | 606/86 R |
| 7,207,949 B2 * | 4/2007 | Miles | A61B 5/0488 |
| | | | 600/214 |
| 7,261,688 B2 | 8/2007 | Smith et al. | |
| 7,582,058 B1 | 9/2009 | Miles et al. | |
| 7,691,057 B2 | 4/2010 | Miles et al. | |
| 7,811,303 B2 * | 10/2010 | Fallin | A61B 17/3417 |
| | | | 606/191 |
| 7,819,801 B2 | 10/2010 | Miles et al. | |
| 7,905,840 B2 | 3/2011 | Pimenta et al. | |
| 7,909,830 B2 * | 3/2011 | Frigg | A61B 17/7002 |
| | | | 606/104 |
| 8,002,798 B2 * | 8/2011 | Chin | A61B 17/7037 |
| | | | 606/246 |
| 8,137,284 B2 * | 3/2012 | Miles | A61B 1/32 |
| | | | 600/554 |
| 8,192,437 B2 * | 6/2012 | Simonson | A61B 17/0218 |
| | | | 606/279 |
| 8,251,997 B2 * | 8/2012 | Michelson | A61B 17/025 |
| | | | 606/246 |
| 8,287,597 B1 * | 10/2012 | Pimenta | A61F 2/4611 |
| | | | 623/17.16 |
| 8,303,515 B2 | 11/2012 | Miles et al. | |
| 8,308,805 B2 | 11/2012 | Lynn et al. | |
| 8,313,430 B1 | 11/2012 | Pimenta | |
| 8,355,780 B2 | 1/2013 | Miles et al. | |
| 8,430,813 B2 | 4/2013 | Selover et al. | |
| 8,512,343 B2 * | 8/2013 | Dziedzic | A61B 17/7089 |
| | | | 606/86 A |
| 8,568,317 B1 | 10/2013 | Gharib et al. | |
| 8,636,655 B1 | 1/2014 | Childs | |
| 8,679,006 B2 | 3/2014 | Miles et al. | |
| 8,728,162 B2 | 5/2014 | Akyuz et al. | |
| 8,834,507 B2 * | 9/2014 | Mire | A61B 17/3421 |
| | | | 606/191 |
| 8,992,558 B2 | 3/2015 | Stone et al. | |
| 9,066,701 B1 | 6/2015 | Finley et al. | |
| 9,138,217 B2 | 9/2015 | Smith et al. | |
| 9,259,213 B1 * | 2/2016 | O'Hara | A61B 17/025 |
| 9,387,009 B2 * | 7/2016 | Fatone | A61B 5/0492 |
| 9,447,803 B1 * | 9/2016 | Fu | A61B 17/8875 |
| 9,539,012 B2 * | 1/2017 | Landry | A61B 17/1671 |
| 9,579,131 B1 * | 2/2017 | Gustine | A61B 17/705 |
| 2003/0078618 A1 | 4/2003 | Fey et al. | |
| 2003/0083688 A1 * | 5/2003 | Simonson | A61B 17/0218 |
| | | | 606/191 |
| 2003/0083689 A1 * | 5/2003 | Simonson | A61B 17/025 |
| | | | 606/191 |
| 2004/0059339 A1 * | 3/2004 | Roehm, III | A61B 17/1757 |
| | | | 606/90 |
| 2004/0138662 A1 * | 7/2004 | Landry | A61B 17/1604 |
| | | | 606/86 A |
| 2004/0176763 A1 | 9/2004 | Foley et al. | |
| 2005/0004593 A1 * | 1/2005 | Simonson | A61B 17/025 |
| | | | 606/191 |
| 2006/0004398 A1 * | 1/2006 | Binder, Jr. | A61B 17/3417 |
| | | | 606/191 |
| 2008/0183044 A1 | 7/2008 | Colleran et al. | |
| 2009/0018399 A1 | 1/2009 | Martinelli et al. | |
| 2009/0036746 A1 * | 2/2009 | Blackwell | A61B 17/0206 |
| | | | 600/219 |
| 2009/0149857 A1 * | 6/2009 | Culbert | A61B 1/018 |
| | | | 606/80 |
| 2010/0114147 A1 * | 5/2010 | Biyani | A61B 1/32 |
| | | | 606/191 |
| 2010/0317989 A1 | 12/2010 | Gharib et al. | |
| 2012/0238893 A1 | 9/2012 | Farquhar et al. | |
| 2016/0038195 A1 * | 2/2016 | Genovese | A61B 17/7082 |
| | | | 606/79 |
| 2016/0354073 A1 * | 12/2016 | Nel | A61B 17/02 |

* cited by examiner

RETRACTION DEVICES, SYSTEMS, AND METHODS FOR MINIMALLY INVASIVE SPINAL SURGERY

CROSS-REFERENCE TO RELATED APPLICATION

This application claims priority to, and the benefit of, U.S. Provisional Patent Application Ser. No. 62/035,017, filed on Aug. 8, 2014, the entire contents of which are incorporated by reference herein.

TECHNICAL FIELD

The present disclosure relates generally to minimally invasive surgical procedures, and more particularly, to devices, systems, and surgical methods for securing a minimally invasive retractor during minimally invasive orthopedic spine surgery.

BACKGROUND

In recent years, minimally invasive surgical approaches have been applied to orthopedic surgery, and more recently, to spinal surgery. Minimally invasive surgery offers significant advantages over conventional open surgery. Besides the advantages of having smaller skin incisions and reduced scarring, the need for extensive tissue and muscle retraction may be greatly reduced. This leads to significantly reduced post-operative pain, a shorter hospital stay, and a shorter overall recovery period.

In a typical spinal surgery, pedicle screws are implanted into vertebral bodies. With minimally invasive spinal surgery procedures, a guidewire can be utilized to identify target locations on the vertebral bodies for placement of the pedicle screws and guided advancement of surgical instruments to the target locations. Proper placement of the guidewire can be effectuated by inserting a biopsy needle through the skin while using special imaging techniques, such as fluoroscopic or magnetic image guidance. Although guidewires can be useful in conducting spinal surgery, proper placement and removal of the guidewires, and associated surgical instruments such as the biopsy needle, can be time consuming.

Therefore, a continuing need exists for an improved device, an improved system, and an improved method for performing minimally invasive spine surgery.

SUMMARY

The present disclosure is directed to a system for mounting a retractor tube to a spine without a guidewire. The system includes an awl, a first dilator, a retractor tube, and a plurality of pins. The awl includes an elongate body that extends between proximal and distal ends. The proximal end of the awl supports a handle and the distal end has a bone engaging tip adapted to secure the awl to at least one vertebral body of the spine. The first dilator has proximal and distal ends that define a longitudinal axis. The first dilator defines a first longitudinal bore that is adapted to receive the awl. The retractor tube includes a tubular body that extends between proximal and distal ends and includes an inner surface and an outer surface. The inner surface defines a second longitudinal bore that extends through the tubular body of the retractor tube, and the outer surface defines a plurality of channels. The system includes a plurality of pins adapted to be received within the plurality of channels of the refractor tube. The plurality of channels enable the plurality of pins to secure the refractor tube to the at least one vertebral body of the spine.

In embodiments, a diameter of the first longitudinal bore may be greater than a diameter of the elongate body of the awl.

The system may include a second dilator. The second dilator may define a third longitudinal bore therethrough adapted for receiving the first dilator. The second dilator may include an outer surface that defines a spiral groove adapted to engage the inner surface of the retractor tube.

In some embodiments, the awl may include a removable handle. The removable handle may define a fourth longitudinal bore configured to receive a portion of the elongate body of the awl. In some embodiments, the fourth longitudinal bore of the removable handle may define a D-shaped channel adapted to receive a D-shaped extension extending from the proximal end of the elongate body of the awl.

In an embodiment, the first dilator may include an outer surface on the distal end that tapers in a distal direction along the longitudinal axis.

In an embodiment, the distal end of the retractor tube is tapered.

In some embodiments, each pin of the plurality of pins may have a shank and a head wherein the shank may be configured to be received by at least one of the plurality of channels of the retractor tube.

The system may include a screw inserter capable of supporting a retractor and a pedicle screw, wherein the screw inserter may be advanceable within the retractor tube and capable of securing the pedicle screw to a vertebral body.

The system may be provided in the form of a kit.

According to yet another aspect, the present disclosure is directed to a method for selectively mounting a retractor tube to a spine without a guidewire. The method includes securing an awl into a vertebral body of the spine, advancing a first dilator over the awl, advancing a retractor tube over the first dilator, introducing at least two pins through channels defined in an outer surface of the retractor tube and into the vertebral body to secure the retractor tube to the vertebral body, and removing the first dilator and the awl from the retractor tube.

The method may include advancing a second dilator over the awl. The method may involve securing at least one of the at least two pins to a facet of the vertebral body. The method may involve securing at least one of the at least two pins to a transverse process of the vertebral body. The method may include removing the first dilator and the second dilator from the retractor tube. The method may involve advancing a screw inserter supporting a retractor and a pedicle screw into the retractor tube to secure the pedicle screw to the vertebral body. The method may include removing the retractor tube and the at least two pins from the vertebral body while maintaining the retractor and the pedicle screw secured to the vertebral body.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figure 1:
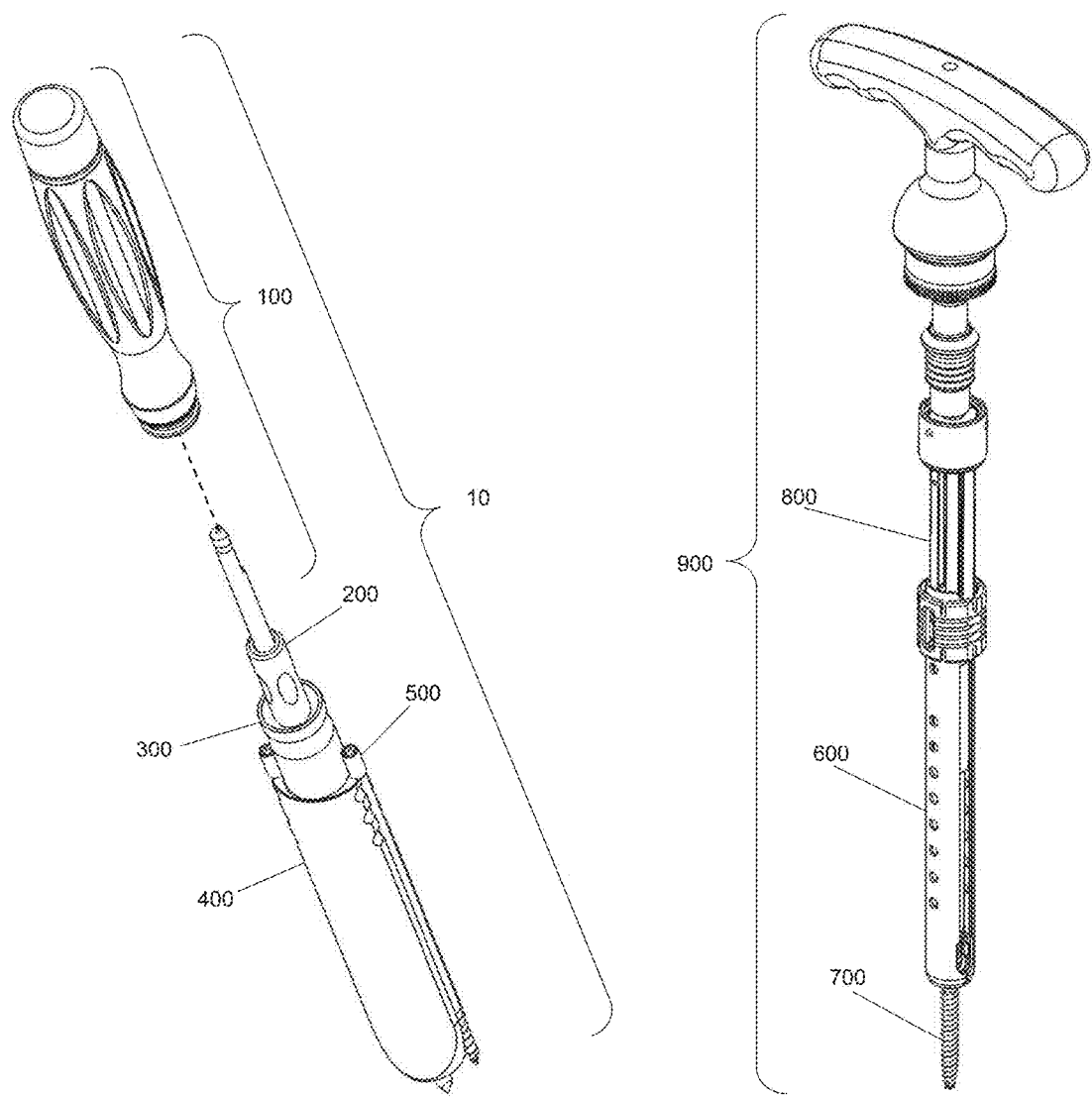
FIG. 1 illustrates a system in accordance with the principles of the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Referring initially to FIG. 1, a first embodiment of the presently disclosed retraction system is illustrated and generally designated as 10.

Retraction system 10 includes an awl 100, a first dilator 200, a second dilator 300, a retractor tube 400, a pair of pins 500, a minimally invasive retractor 600, a pedicle screw 700, and a screw inserter assembly 800.

Figure 2:
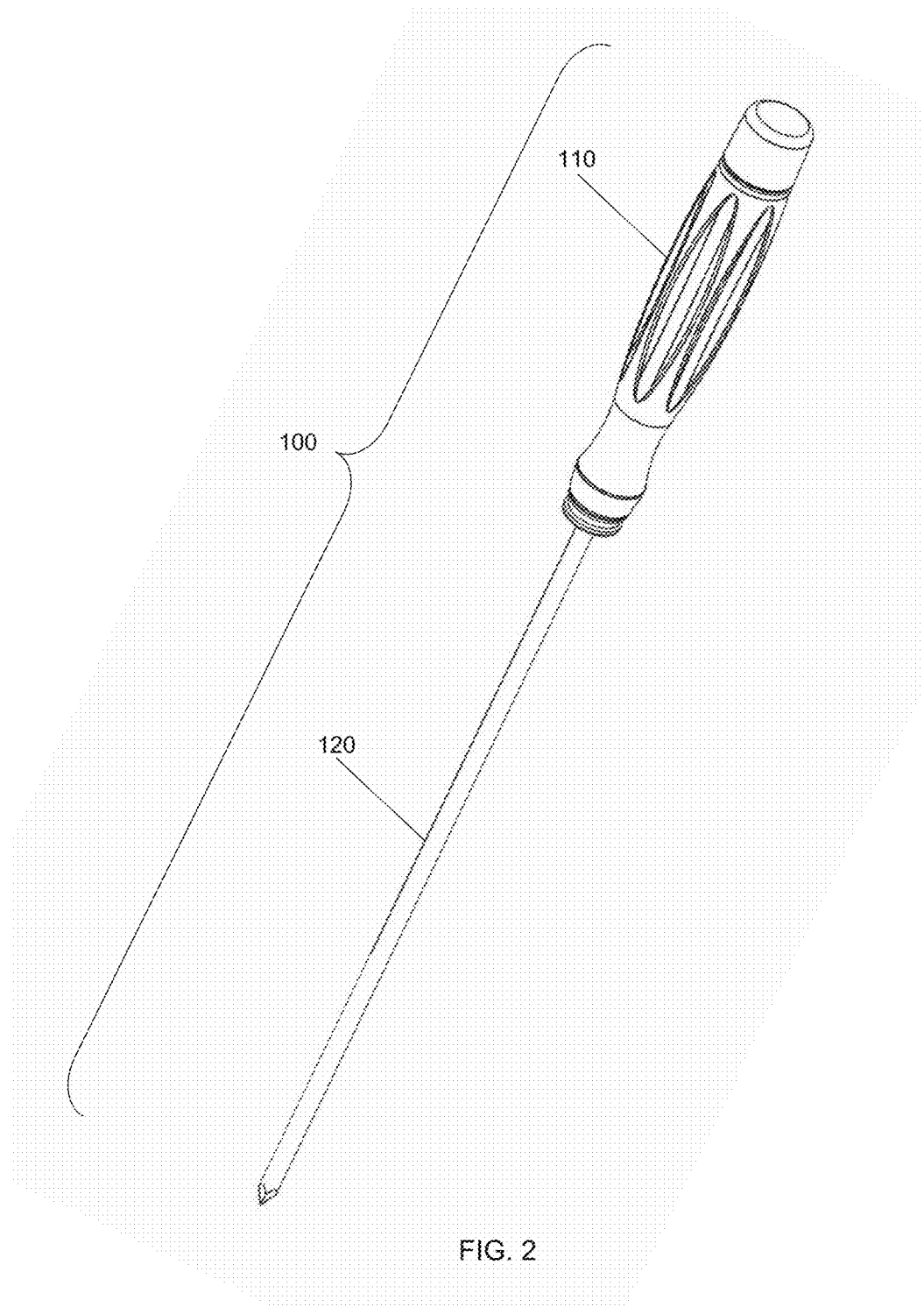
FIG. 2. is a perspective view of an awl of the system of FIG. 1.
Figure 3:
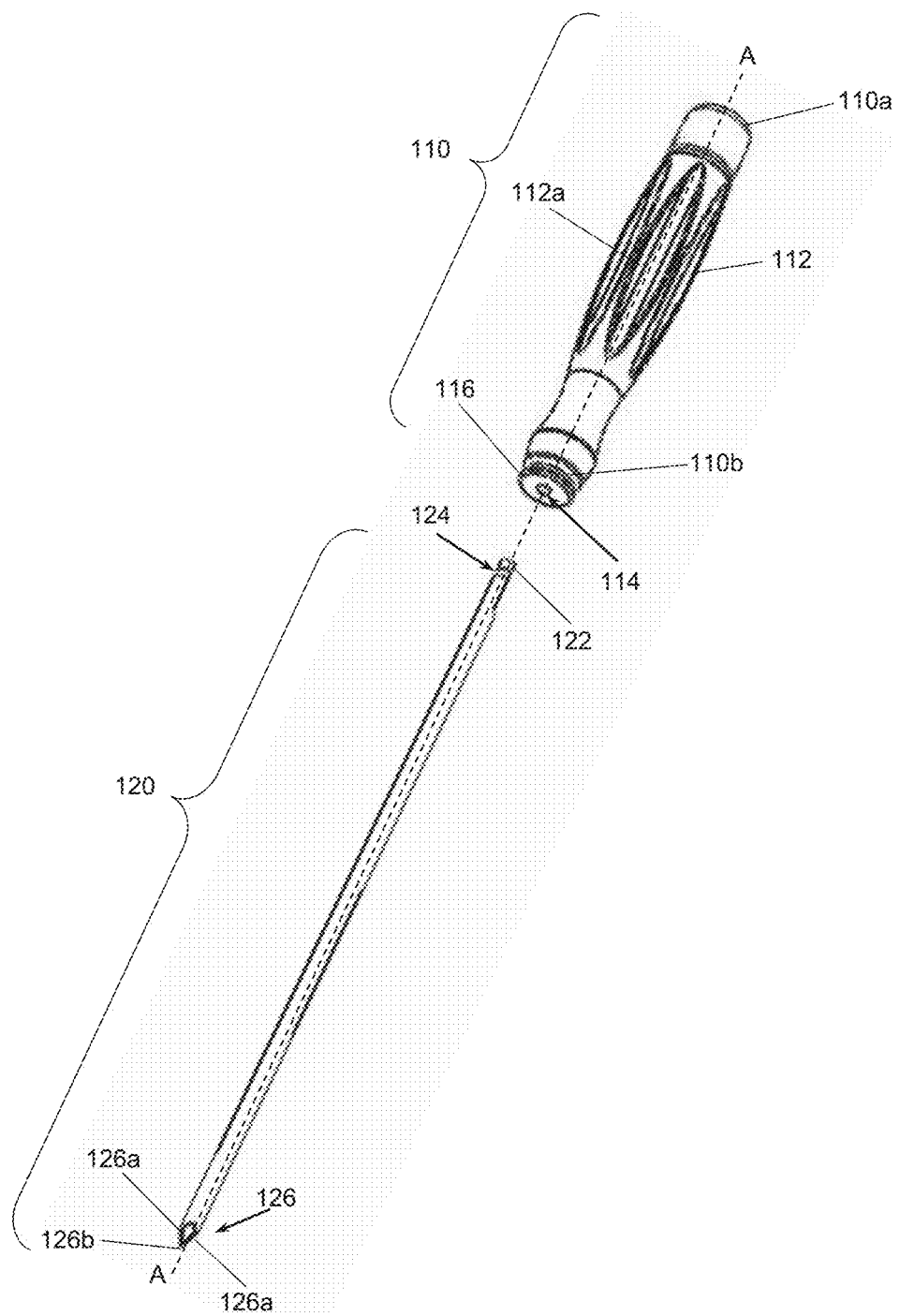
FIG. 3 is a perspective view, with parts separated, of the awl of FIG. 2.

Awl 100, as seen in FIGS. 2 and 3, includes a handle 110 and an elongate body 120. Awl 100 defines a longitudinal axis A-A that extends therethrough. In one embodiment, handle 110 can be fixedly secured to elongate body 120. Handle 110 includes proximal and distal ends 110a, 110b. Handle 110 includes a gripping portion 112 disposed between proximal and distal ends 110a, 110b of handle 110. Gripping portion 112 is adapted to facilitate gripping. Although shown with crenellations 112a, gripping portion 112 can have any suitable shape and/or dimension to facilitate gripping. A longitudinal bore 114 is defined through a proximal end face 116 of handle 110. Longitudinal bore 114 is dimensioned to receive a proximal end of elongate body 120 of awl 100 to connect handle 110 with elongate body 120. Longitudinal bore 114 may have suitable shape and/or dimension to transmit the rotational motion of handle 110 to elongate body 120. In one embodiment, longitudinal bore 114 includes a D-shape profile. In embodiments, handle 110 and elongate body 120 are securable together in frictional arrangement.

Elongate body 120 includes an engagement section 122 at a proximal end thereof that is configured to be received within longitudinal bore 114 of handle 110. Engagement section 122 may have any suitable shape and/or dimension, which corresponds to the bore 114, such as a D-shape. An annular groove 124 is defined in elongate body 120 adjacent to engagement section 122. A distal end of elongate body 120 terminates in a pointed tip 126. Pointed tip 126 can have any shape and/or dimension suitable to penetrate a patient's skin and/or bone such as a vertebral body. In one embodiment, pointed tip 126 includes a plurality of facets 126a which taper distally along and radially inward towards axis A-A such that the plurality of facets 126a intersect and terminate in a sharp point 126b. The plurality of facets 126a further facilitate penetration of skin and/or bone.

Figure 4:
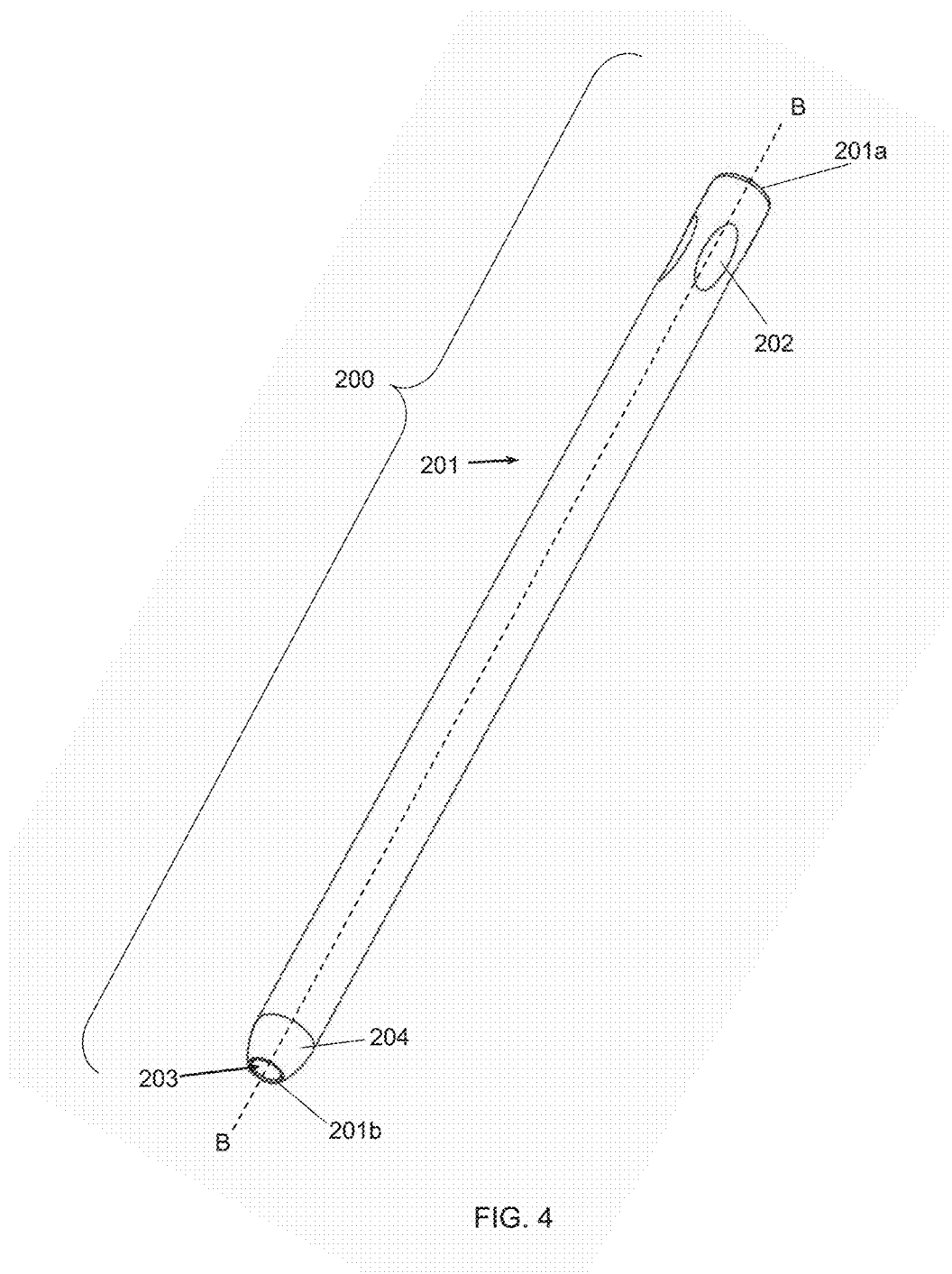
FIG. 4 is a perspective view of a first dilator of the system of FIG. 1.

Referring now to FIG. 4, an embodiment of first dilator 200 is illustrated. First dilator 200 includes an elongate body 201. Elongate body 201 includes proximal and distal ends, 201a, 201b, and defines a longitudinal axis B-B that extends therethrough. A longitudinal bore 203 is defined by internal surfaces of elongate body 201. Longitudinal bore 203 extends between the proximal and distal ends 201a, 201b of elongate body 201. Longitudinal bore 203 is generally shown as having a circular cross section; however, longitudinal bore 203 may have any suitable cross section, such as rectangular, square, hexagonal, etc. Inner surfaces of elongate body 201 can be complimentary to elongate body 120 of awl 100 such that first dilator 200 may advance thereover for aligning the longitudinal axes of first dilator 200 and awl 100 (i.e., coaxially). Distal end 201b of elongate body 201 includes a taper 204 that transitions radially inward, toward and distally along, axis B-B. In one embodiment, taper 204 is curvate. In another embodiment, a proximal portion of elongate body 201 of first dilator 200 includes gripping portion 202. Gripping portion 202 is adapted to facilitate gripping. Although shown with crenellations, gripping portion 202 can have any suitable shape and/or dimension to facilitate gripping.

Figure 5:
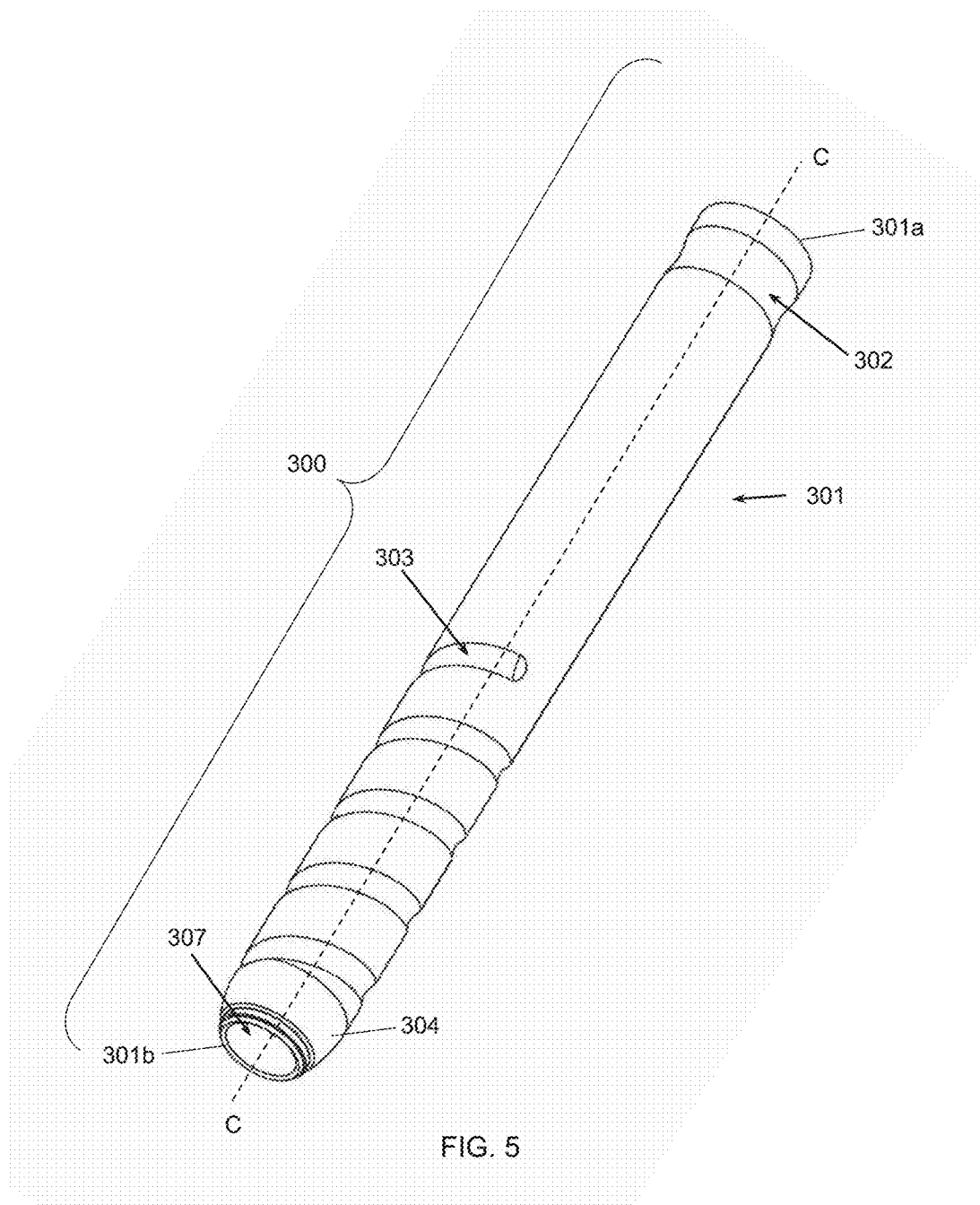
FIG. 5 is a perspective view of a second dilator of the system of FIG. 1.

FIG. 5 illustrates second dilator 300. Second dilator 300 includes an elongate body 301. Elongate body 301 includes proximal and distal ends 301a, 301b, and defines a longitudinal axis C-C that extends therethrough. A longitudinal bore 307 is defined by inner surfaces of second dilator 300. Longitudinal bore 307 extends between the proximal and distal ends 301a, 301b of second dilator 300. Longitudinal bore 307 is generally shown as having a circular cross section; however, longitudinal bore 307 may have any suitable cross section such as rectangular, square, hexagonal, etc. In embodiments, inner surfaces of second dilator 300 can be complementary to outer surfaces of elongate body 201 of first dilator 200 such that second dilator 300 may advance thereover for aligning the longitudinal axes of first and second dilators 200, 300 (i.e., coaxially). An annular groove 302 is defined in elongate body 201 adjacent to proximal end 301a and is adapted to facilitate gripping. Although shown as having a circular profile, annular groove 302 can have any suitable shape and/or dimension to facilitate gripping. A distal portion of elongate body 301 defines a spiral groove 303 in the outer surface thereof. Spiral groove 303 extends along axis C-C. Distal end 301b of elongate body 301 includes a taper 304, that transitions radially inward, toward and distally along, axis C-C. In one embodiment, taper 304 is curvate.

Figure 6:
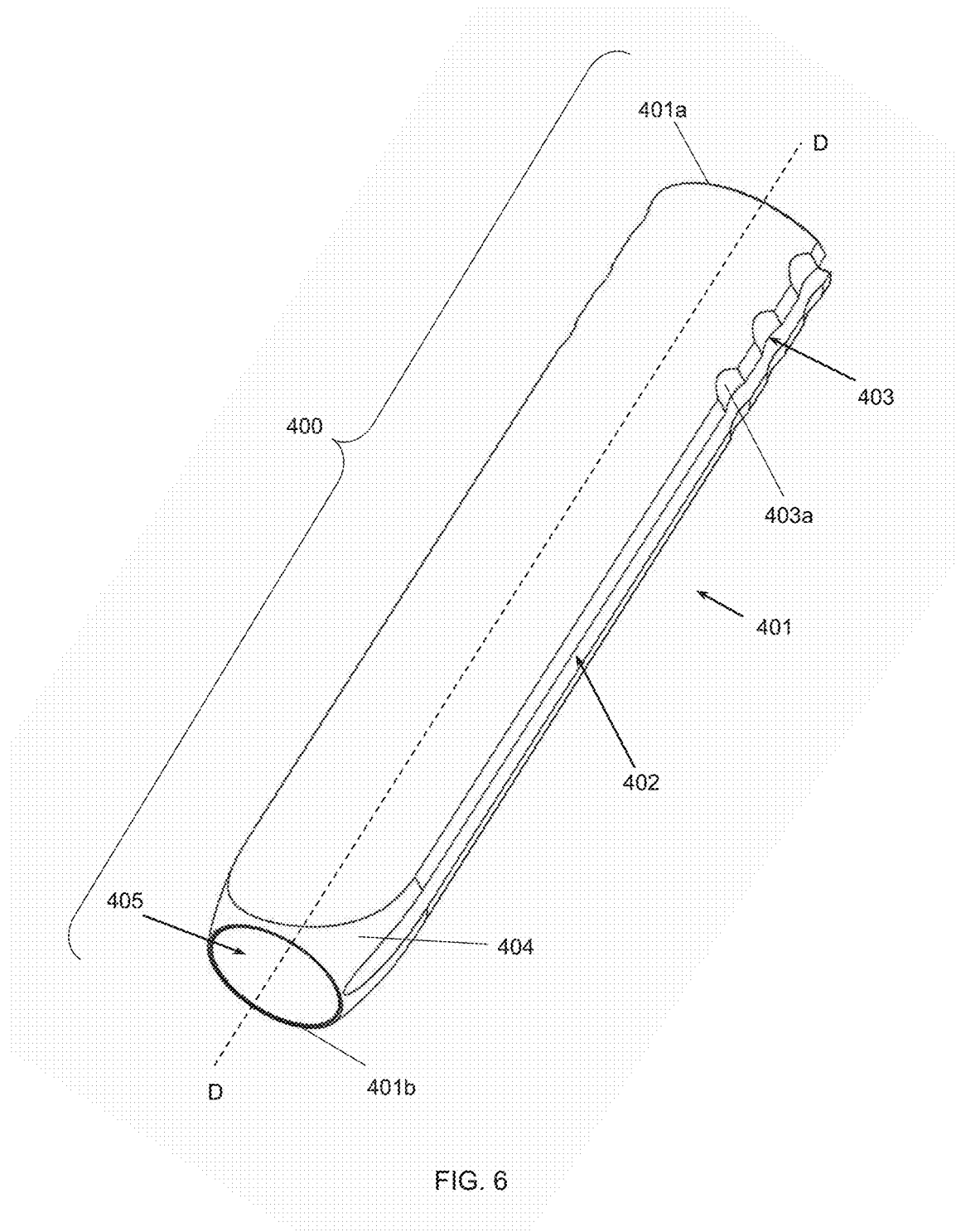
FIG. 6 is a perspective view of a retractor tube of the system of FIG. 1.

Referring now to FIG. 6, an embodiment of retractor tube 400 is illustrated. Retractor tube 400 includes an elongate body 401. Elongate body 401 includes proximal and distal ends 401a, 401b, and defines a longitudinal axis D-D that extends therethrough. Elongate body 401 is generally shown as having an oval cross section; however, elongate body 401 may have any suitable cross section such as rectangular, square, hexagonal, or the like. A longitudinal bore 405 is defined by inner surfaces of retractor tube 400. Longitudinal bore 405 extends between the proximal and distal ends 401a, 401b of retractor tube 400. Longitudinal bore 405 is generally shown as having a circular cross section; however, longitudinal bore 405 may have any suitable cross section such as rectangular, square, hexagonal, etc. In embodiments, inner surfaces of retractor tube 400 can be complementary to outer surfaces of elongate body 301 of second dilator 300 for aligning the longitudinal axes of second dilator and retractor tube 300, 400 (i.e., coaxially).

Figure 7:
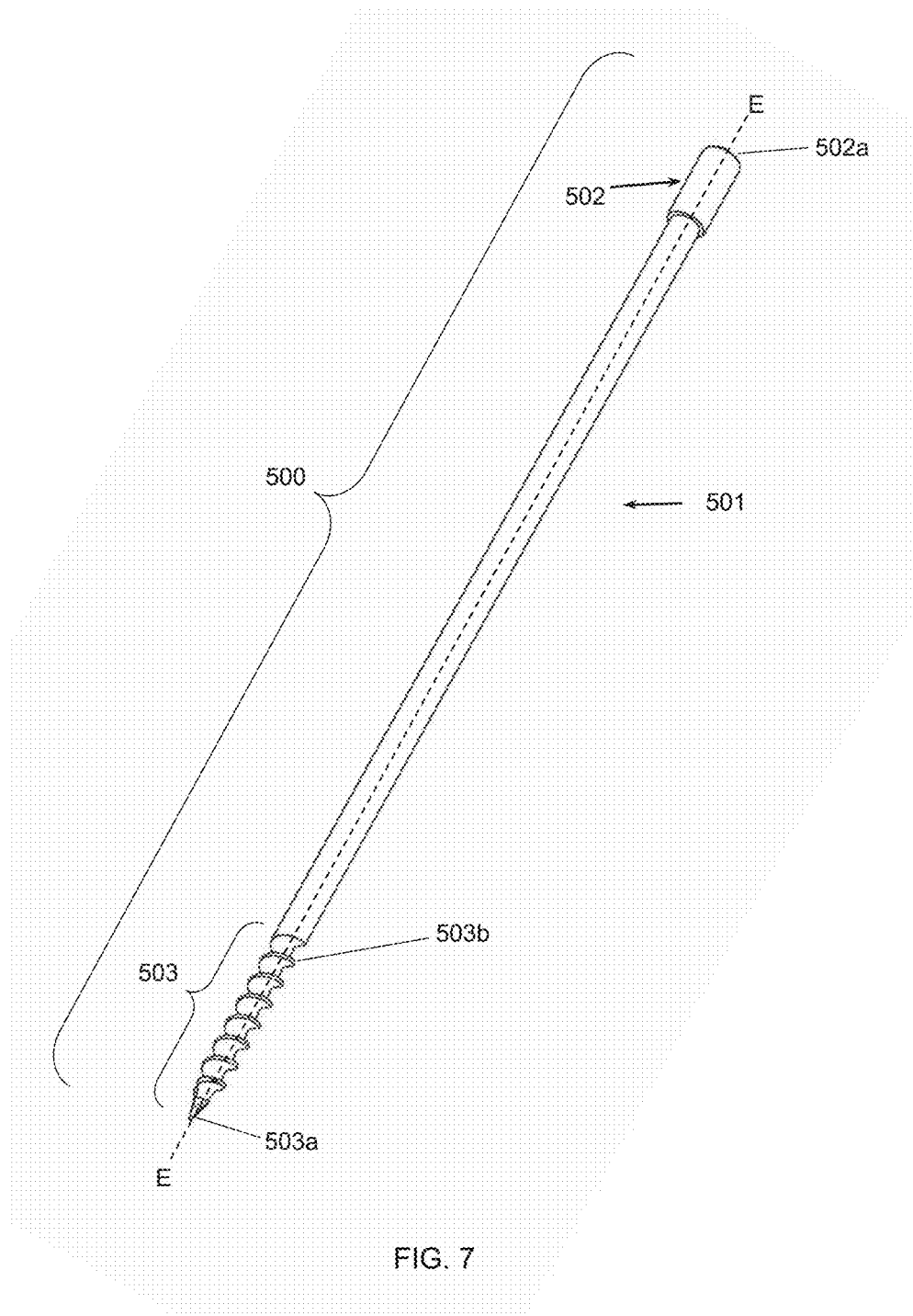
FIG. 7 is a perspective view of a pin of the system of FIG. 1.
Figure 16:
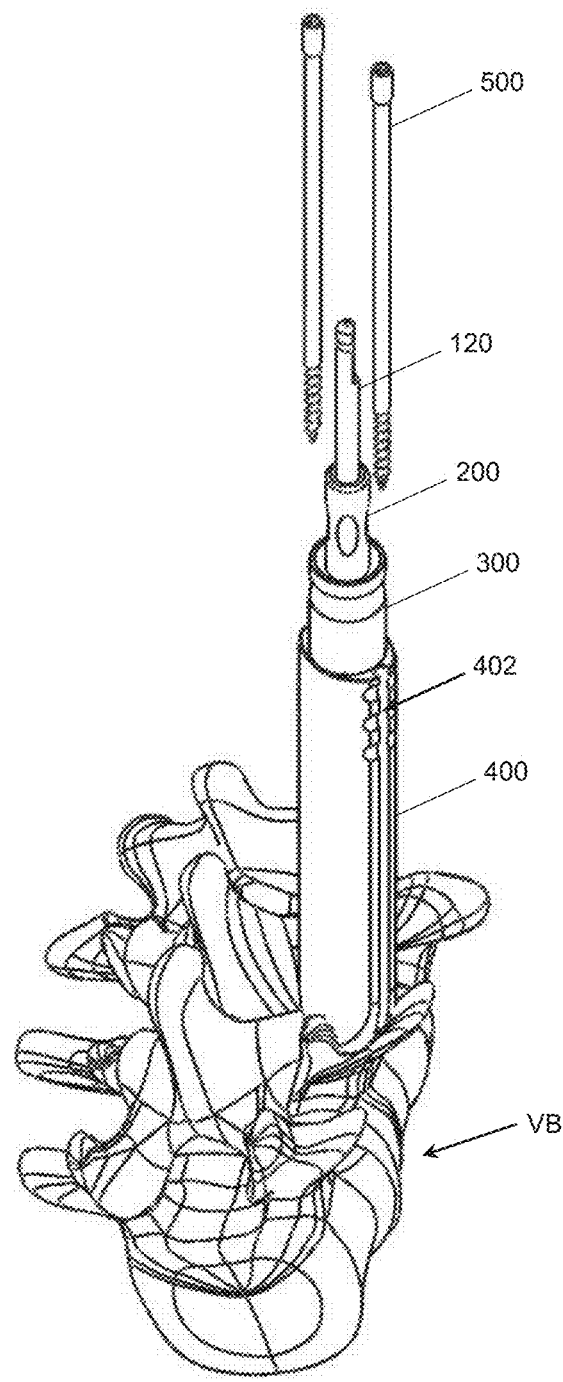

The distal end 401b of elongate body 401 includes a taper 404 that transitions radially inward, toward and distally along, axis D-D and includes a notch for engaging a boney landmark structure (e.g., a facet) to orient retractor tube 400 (FIG. 16). In one embodiment, taper 404 is curvate. Channels 402 are defined through the outer surface of elongate body 401 on opposing sides thereof. Channels 402 extend between proximal and distal ends 401a, 401b and are adapted to receive a pair of pins 500 (FIG. 7). Each channel 402 includes a cross section having the shape of an interrupted circle (i.e., channel 402 has arcuate sides extending greater than halfway around the circumference of the circle), and is adapted to frictionally engage a pin 500 therein such that the pin 500 can only translate axially in the channel 402. Elongate body 401 includes gripping portion 403 adjacent to proximal end 401a that is adapted to facilitate gripping. Although shown with crenellations 403a, gripping portion 403 can have any suitable shape and/or dimension to facilitate gripping.

FIG. 7 illustrates an embodiment of pin 500. Pin 500 includes an elongate body 501. Elongate body 501 includes a head 502 on a proximal end thereof and a self-drilling tip 503a on a distal end. Elongate body 501 defines a longitudinal axis E-E therethrough. Head 502 is configured and/or dimensioned to engage the proximal end 401a of retractor tube 400 and limit axial translation of elongate body 501 through retractor tube 400. The proximal end of head 502 includes a tool engaging portion 502a that can be adapted to cooperate with any tool known in the art. Tool engaging portion 502a may have any shape and/or dimension suitable for transmitting rotational motion from a tool to pin 500, such as square, hex, pozidrive, or the like. A distal end of elongate body 501 includes a threaded shank 503 extending distally along axis E-E. Threaded shank 503 includes threads 503b and terminates in self-drilling tip 503a. Self-drilling tip 503a can have any shape and/or dimension suitable to penetrate and engage bone such as a vertebral body. Pin 500 is adapted to securely fasten retractor tube 400 to a vertebral body VB.

Figure 8:
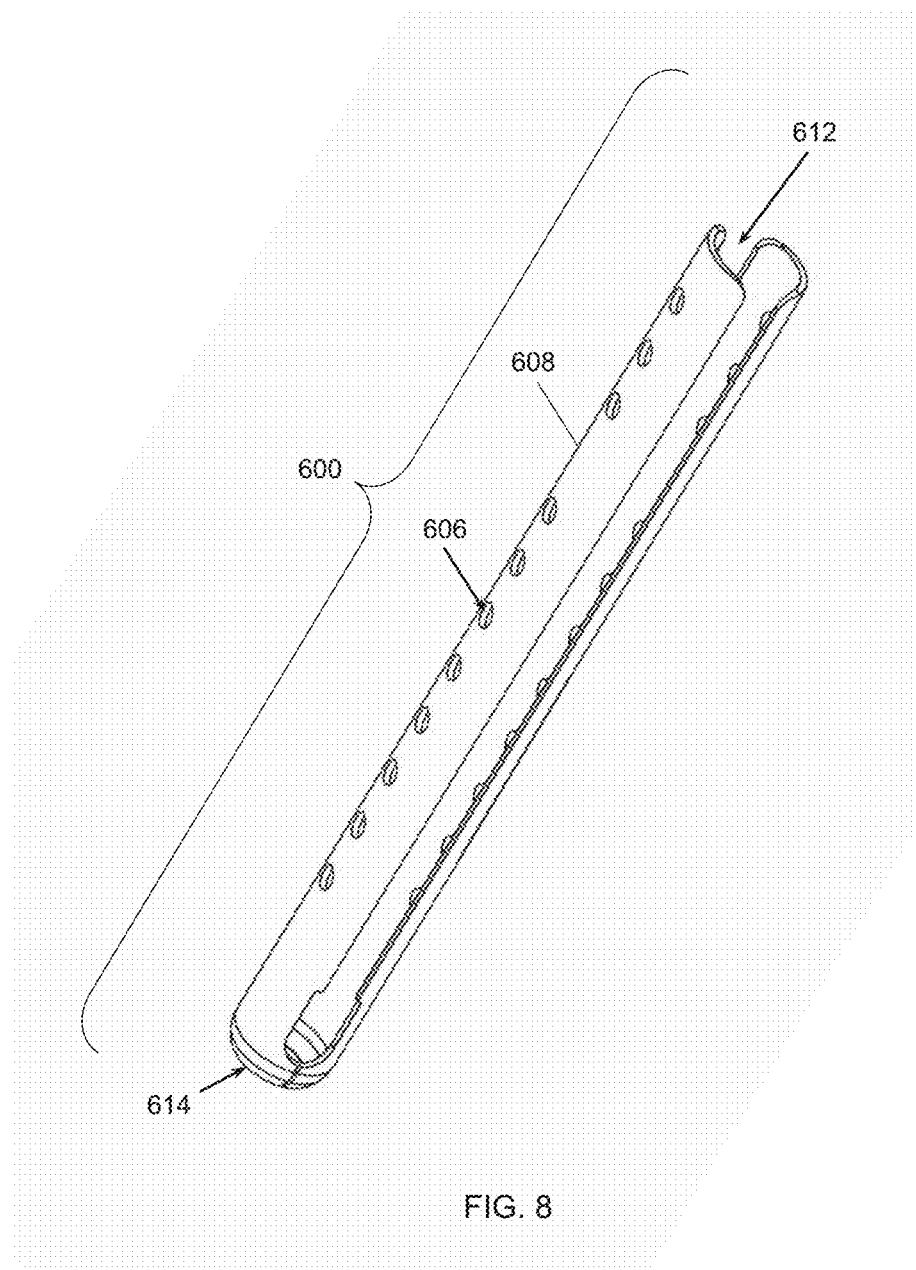
FIG. 8 is a side view of a retractor of the system of FIG. 1.

In FIG. 8, a retractor 600 is illustrated. Retractor 600 is constructed of a flexible material and includes an open proximal end 612 and an open distal end 614 that are disposed in communication with one another. Additionally, retractor 600 includes a pair of opposed refractor blades 608 that define a plurality of instrument holes 606. Instrument holes 606 are configured and/or dimensioned to cooperate with different surgical instruments (e.g., Gelpi retractor). Open distal end 614 is sized to receive a shank 703 of pedicle screw 700 (FIG. 9) therethrough and inhibit passage of a tulip 702 of pedicle screw 700 for supporting pedicle screw 700 at distal end 614 of retractor 700.

For a detailed discussion of the construction of retractor 600, reference may be made to U.S. Pat. No. 8,298,138, filed on Nov. 8, 2010, entitled "Minimally Invasive Refractor and Methods of Use," the entire contents of which are incorporated herein by reference.

Figure 9:
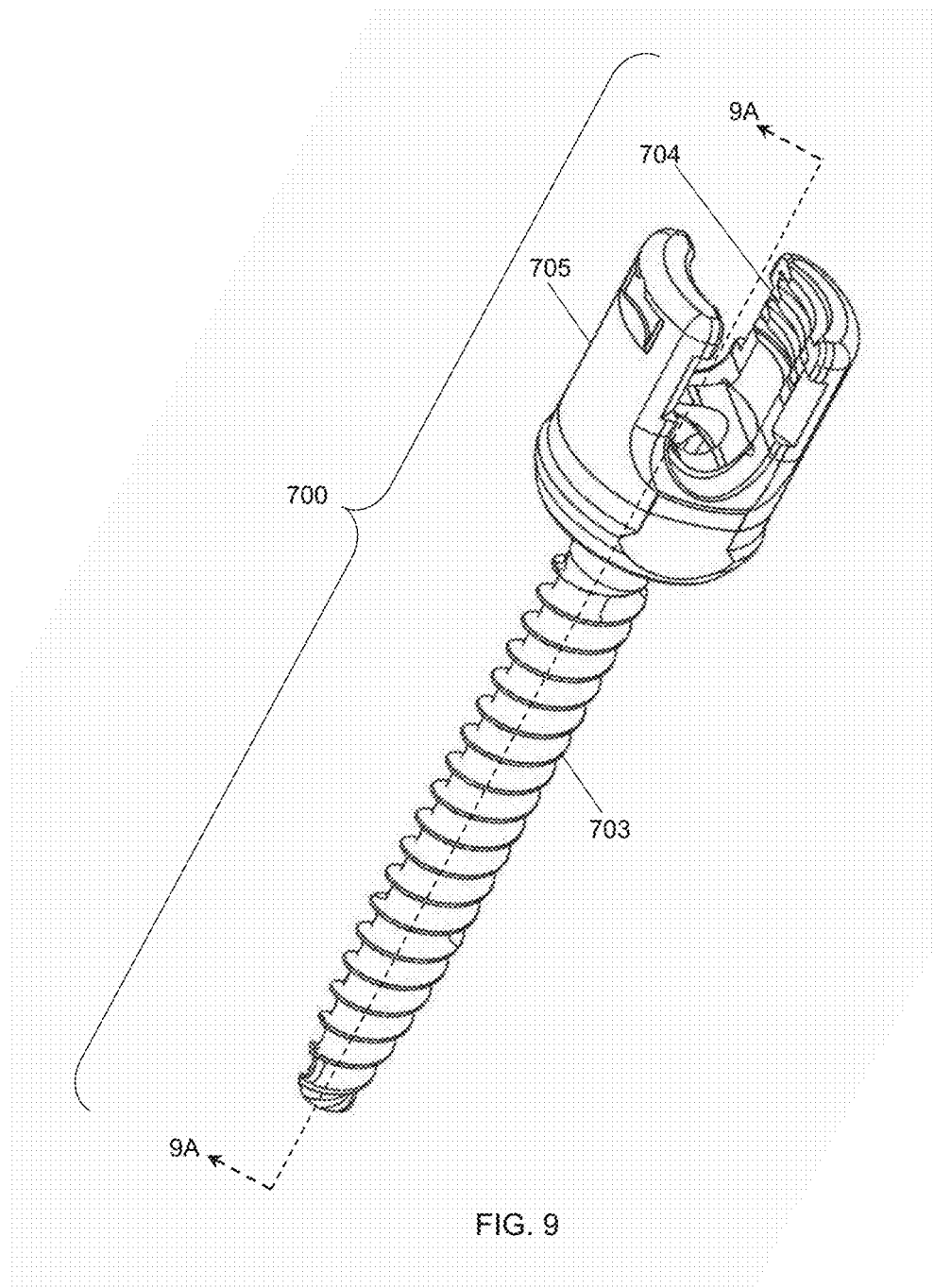
FIG. 9 is a perspective view of a pedicle screw of the system of FIG. 1.
Figure 9A:
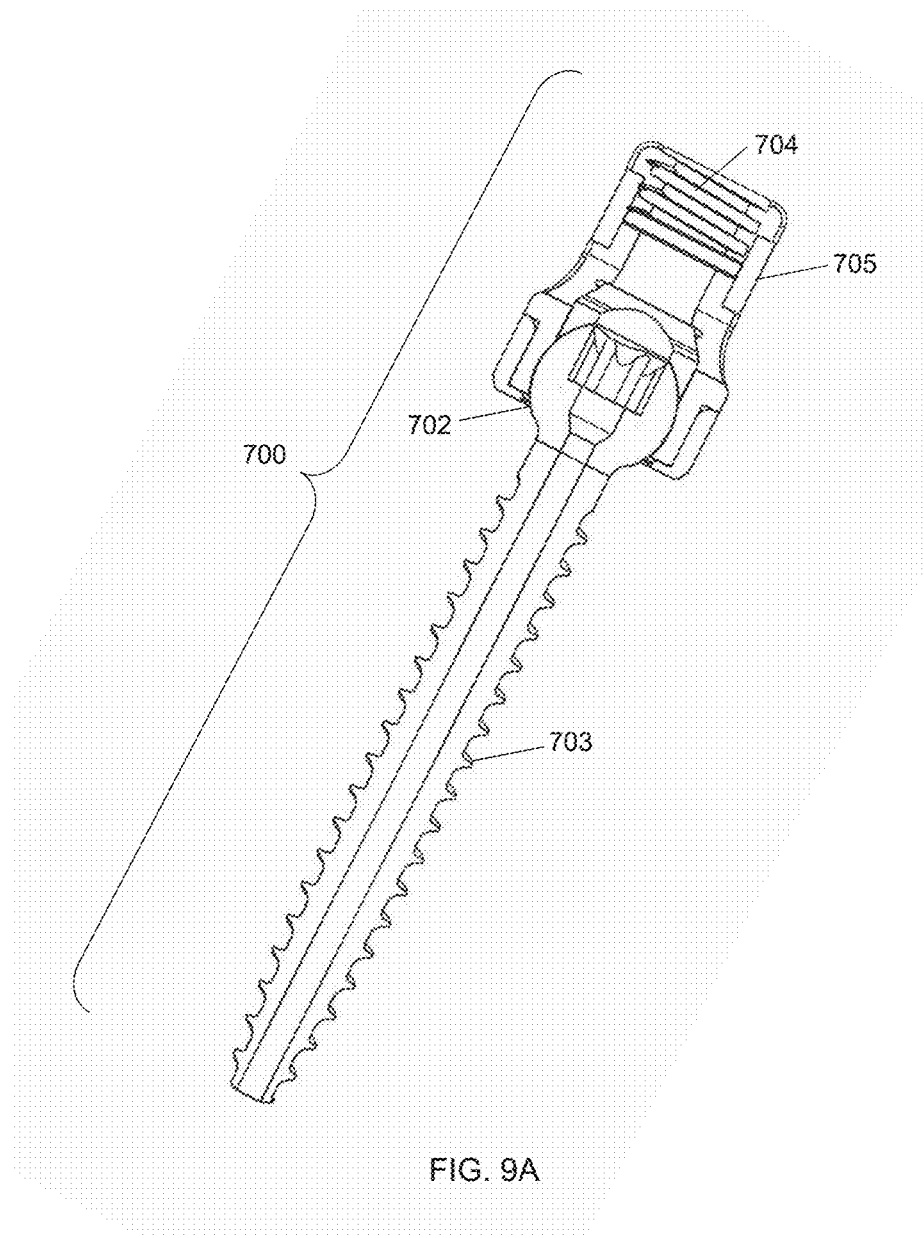
FIG. 9A is a cross-sectional view of the pedicle screw of FIG. 9 taken along section line 13B-13B.

Referring now to FIGS. 9 and 9A, one embodiment of pedicle screw 700 is illustrated. Pedicle screw 700 includes a tulip 705, head 702 (FIG. 9A), and a threaded shank 703 extending distally therefrom. Threaded shank 703 is configured and dimensioned to pass through distal end 614 of retractor 600. Tulip 705 has a diameter dimensioned to prevent passage of pedicle screw 700 through distal end 614 of retractor 600. Head 702 includes a tool engaging portion that is adapted to cooperate with a screw inserter 900. The tool engaging portion may have any suitable shape and/or dimension for transmitting the rotational motion of screw inserter 900 to head 702, such as square, hex, pozidrive, or the like. Tulip 705 includes a threaded portion 704 that is adapted to removably attach to screw inserter 900.

For a detailed discussion of the construction of exemplary pedicle screws, reference may be made to U.S. Patent Application Publication No. 2013/0013003, filed on Sep. 26, 2012, entitled "Polyaxial Bonescrew Assembly," and U.S. Patent Application Publication No. 2012/0022598, filed Sep. 29, 2011, entitled "Spinal Fixation System," the entire contents of each which are incorporated herein by reference.

Figure 10:
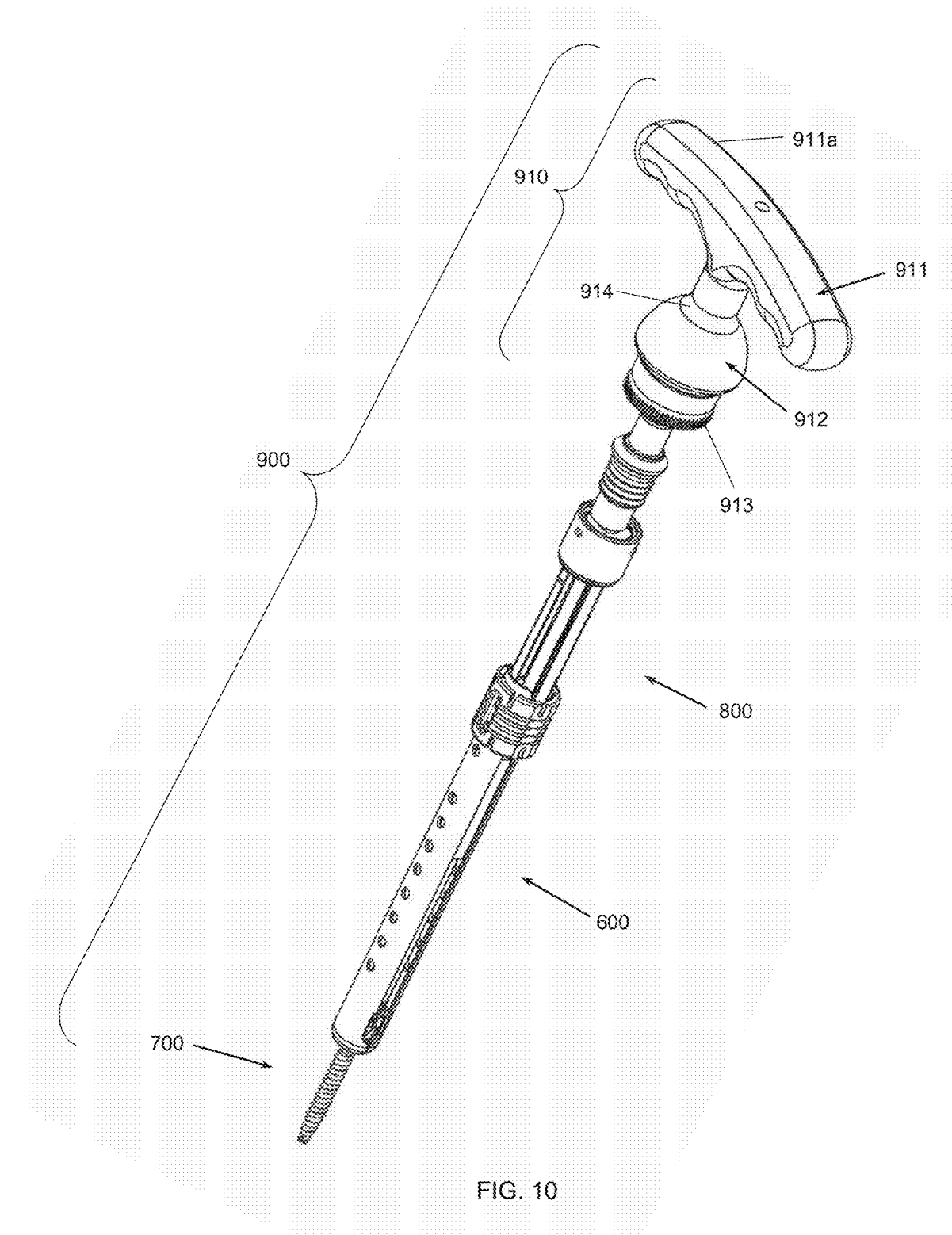
FIG. 10 is a perspective view of a screw inserter of the system of FIG. 1 coupled with the pedicle screw.
Figure 11:
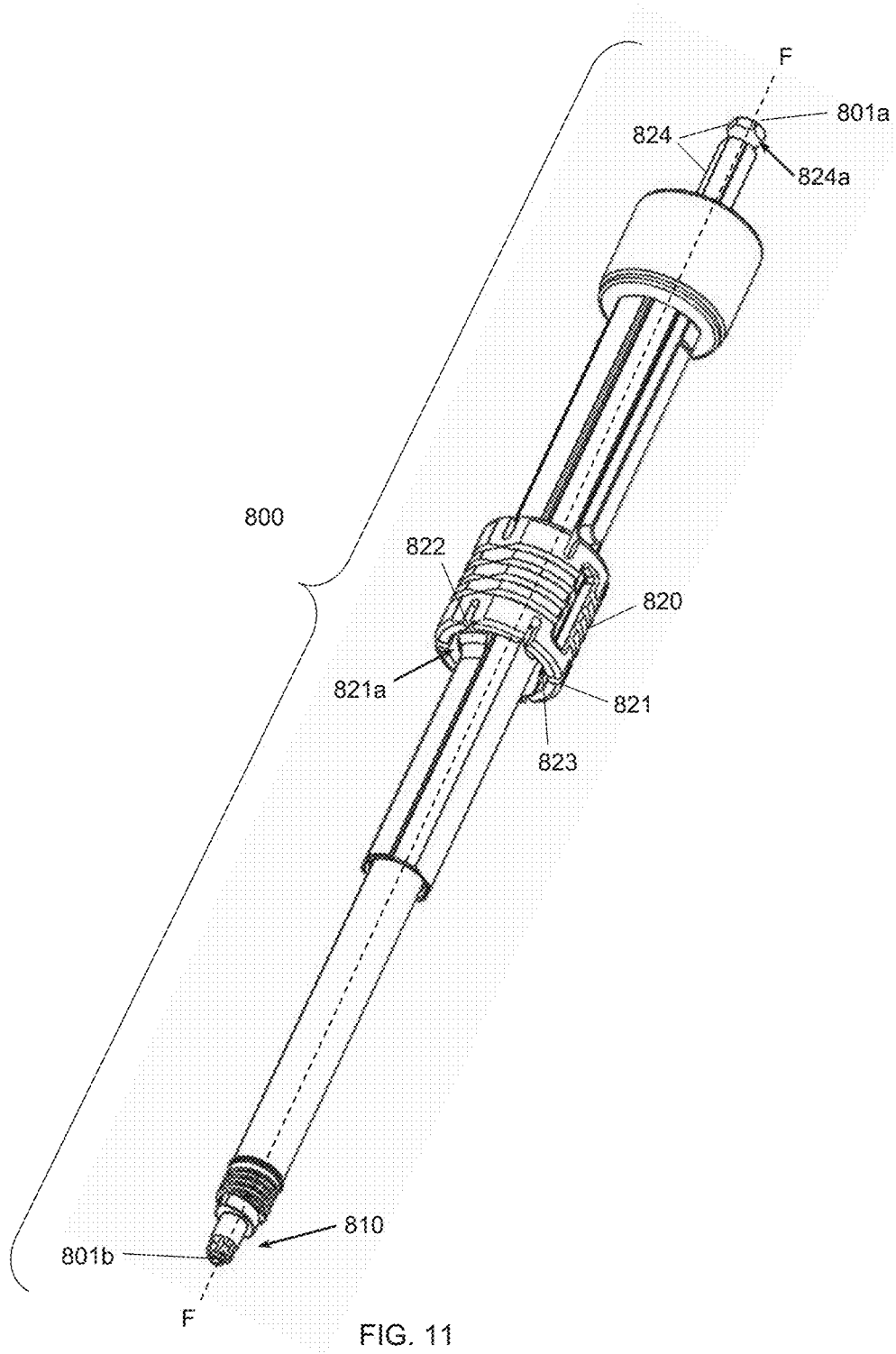
FIG. 11 is a perspective view of the screw inserter of FIG. 10 with a screw inserter handle removed for clarity.

FIGS. 10 and 11 disclose a screw inserter 900. Screw inserter 900 includes a handle assembly 910 and a screw inserter assembly 800. As shown in FIG. 11, screw insertion assembly 800 includes proximal and distal ends 801a, 801b, and defines longitudinal axis F-F therethrough. Distal end 801b includes a tool engaging portion 810 and is configured and/or dimensioned to engage the tool engaging portion of head 702 of pedicle screw 700. Collar 820 is disposed between the proximal and distal ends 801a, 801b, of screw inserter assembly 800. Collar 820 is generally shown having a circular cross section; however, collar 820 may have any suitable cross section such as rectangular, square, hexagonal, etc. In embodiments, collar 820 can be complementary to inner surfaces of retractor tube 400 for aligning the longitudinal axes of screw inserter assembly 800 and retractor tube 400. Collar 820 defines a longitudinal bore 821 having a diameter greater than that of screw inserter assembly 800 such that an annular space 821a is defined therebetween. Annular space 821a is divided into two portions by protrusions 822, 823 that extend radially outward from axis F-F and are oriented 180 degrees apart about axis F-F Annular space 821a and protrusions 822, 823 operate in conjunction such that retractor 600 may be advanced within annular space 821a whereby protrusions 822, 823 are disposed between each retractor blade 608. When fully advanced within annular space 821a, retractor 600 is prohibited from rotating about axis F-F with respect to screw inserter assembly 800. Collar 820 prevents retractor blades 608 from spreading apart, thereby allowing screw inserter 900 to be fully advanced within longitudinal bore 405 of retractor tube 400.

Proximal end 801a of screw inserter assembly 800 includes a hexagonal cross section 824 configured and/or dimensioned to be in mechanical cooperation with the distal end of handle assembly 910 such that screw inserter assembly 800 is prevented from axially and/or rotationally translating relative to handle assembly 910 (see FIG. 10).

Handle assembly 910, as illustrated in FIG. 10, includes a T-shaped member 911, a tubular body 914, a ratchet assembly 912, and selection mechanism 913. T-shaped member 911 includes elongate body 911a and the tubular body 914 extends in a direction normal to elongate body 911a such that elongate body 911a is bisected, thereby forming T-shaped member 911. Tubular body 914 extends longitudinally relative to axis F-F and is configured and/or dimensioned to engage hexagonal cross 824 of screw insertion assembly 800.

In operation, a clinician may selectively engage screw inserter assembly 800 by moving selection mechanism 913 to a first position or a second position by rotating selection mechanism 913 in a clockwise or counterclockwise direction. Ratchet assembly 912 permits selective engagement of handle assembly 912 to screw inserter assembly 800 such that rotation of handle assembly 912 in one direction causes screw inserter assembly 800 to rotate therewith. Rotation of handle assembly 912 in an opposite direction does not cause screw inserter assembly 800 to rotate. Selection mechanism 913 can be rotated between a first position that enables rotation in a first direction, and a second position, enabling rotation in second, opposite direction.

Another embodiment of screw inserter 900 is disclosed in U.S. Pat. No. 8,298,138, filed on Nov. 8, 2010, entitled "Minimally Invasive Retractor and Methods of Use," the entire contents of which are incorporated herein by reference.

It is further contemplated that two or more components of the retraction system 10 as disclosed herein may be provided in the form of a kit.

Figure 12:
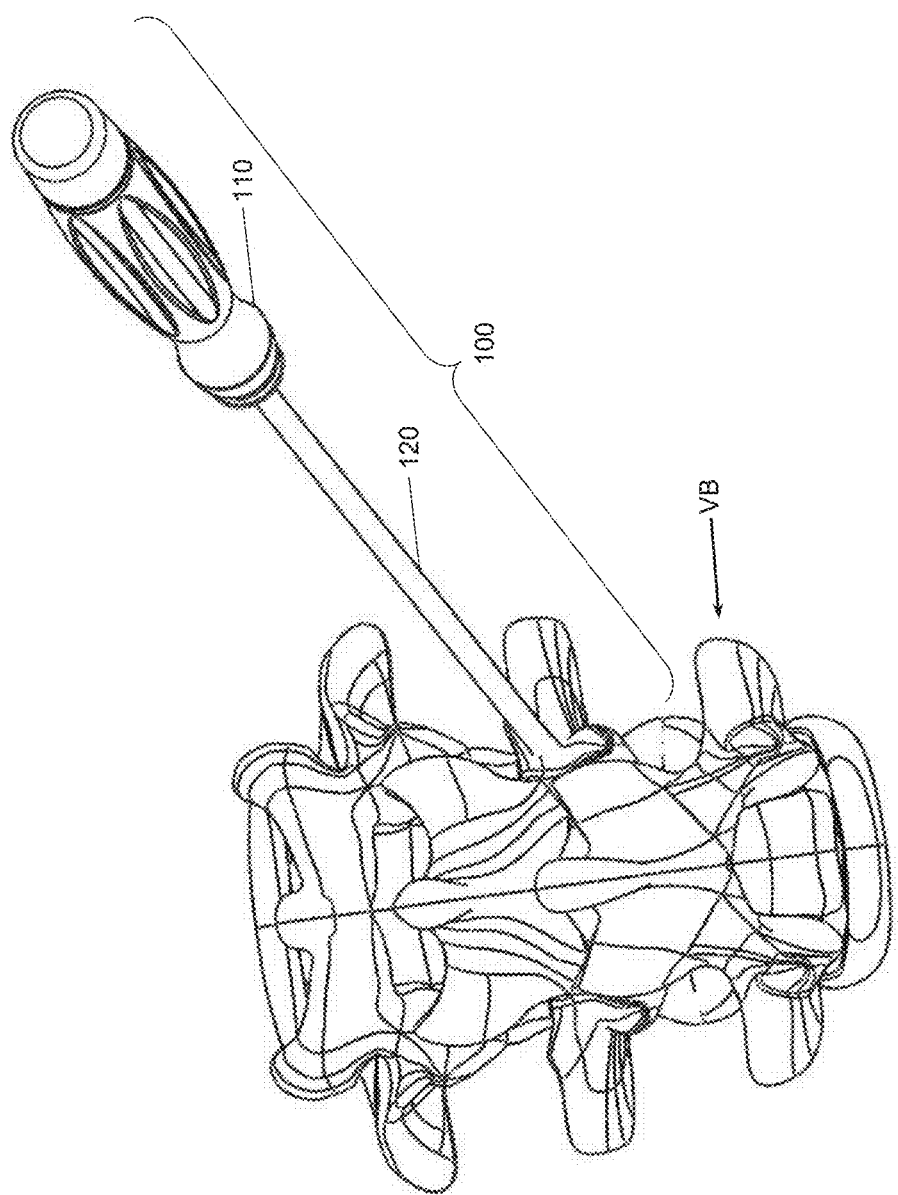
FIGS. 12-21 are progressive views illustrating a securement of the retractor with a pedicle screw to a vertebral body.
Figure 13:
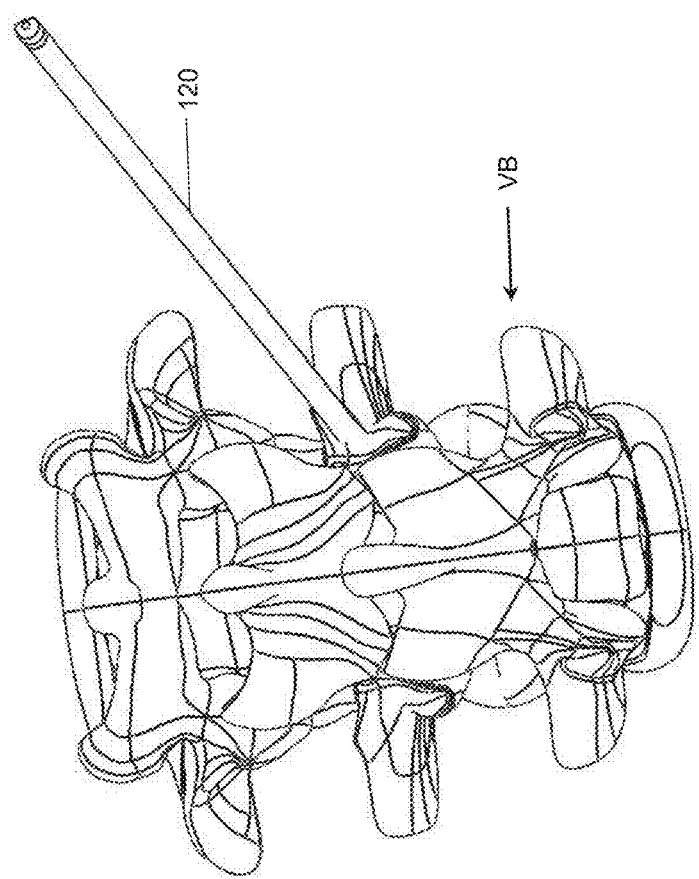
Figure 14:
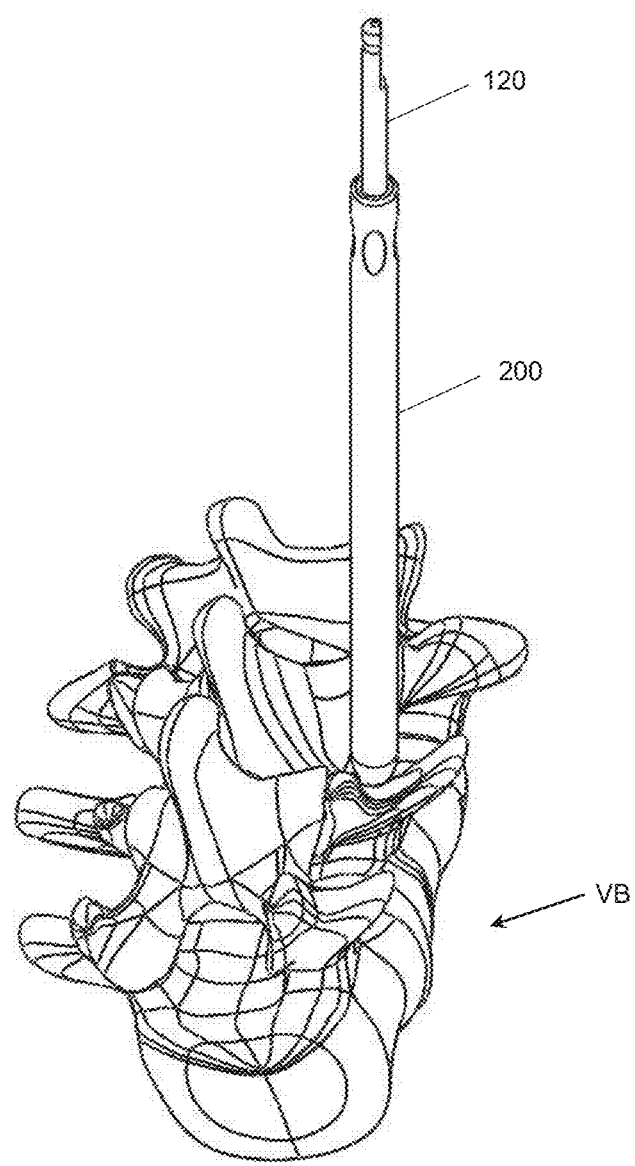
Figure 15:
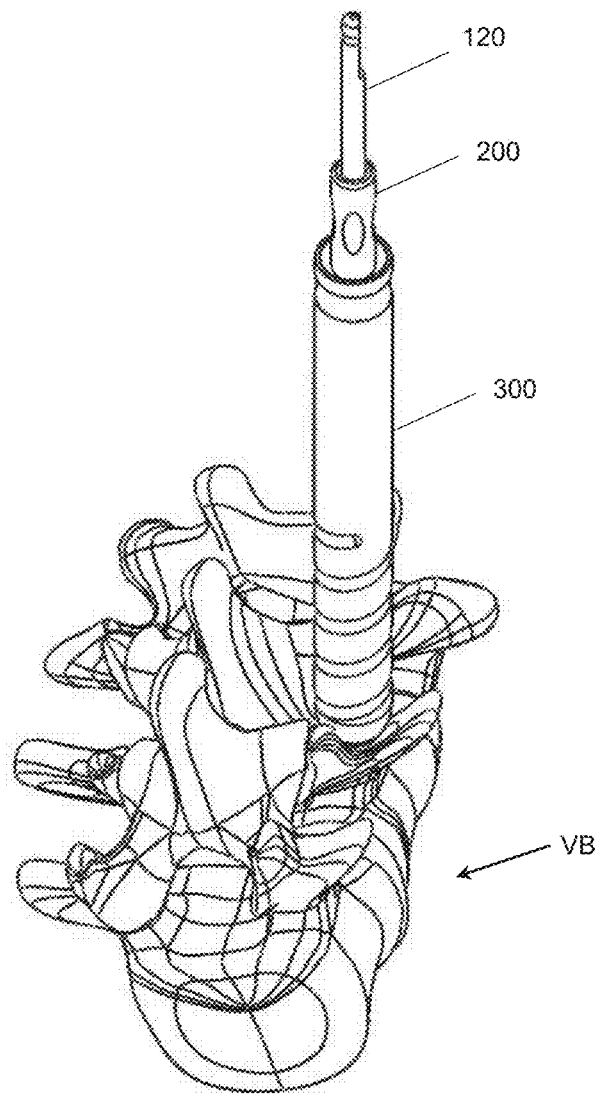

In operation, a clinician employs retraction system 10 to secure a pedicle screw to a vertebral body "VB" (see FIGS. 12-21). Initially, the clinician cannulates the pedicle of vertebral body "VB" using awl 100 from a percutaneous approach as shown in FIG. 12. The clinician next removes handle 110 from awl 100 such that elongate body 120 remains fixed to vertebral body "VB" as illustrated in FIG. 13. Next, the clinician may advance first dilator 200 over elongate body 120 of awl 100 such that distal end 201b of first dilator 200 is fully seated against vertebral body "VB" as in FIG. 14. By advancing first dilator 200 over elongate body 120, the skin and other soft tissue of the patient is stretched to accommodate the increased diameter of first dilator 200. The clinician may next advance second dilator 300 over first dilator 200 such that distal end 301b of second dilator 300 is fully seated against vertebral body "VB" as illustrated in FIG. 15. Advancing second dilator 300 over first dilator 200 further stretches the skin and other soft tissue to accommodate the increased diameter of second dilator 300.

Next, the clinician may advance retractor tube 400 over second dilator 300 such that distal end 401b of retractor tube 400 is fully seated against vertebral body "VB" as illustrated in FIG. 16. In one embodiment, first dilator 200 may include a diameter equal to that of longitudinal bore 405 of retractor tube 400, whereby second dilator 300 may not be needed. Retractor tube 400 is generally shown as being oriented such that channel 402 is situated above a transverse process of vertebral body "VB". However, retractor tube 400 may be oriented such that channel 402 is situated above a facet or a transverse process of vertebral body "VB".

Figure 17:
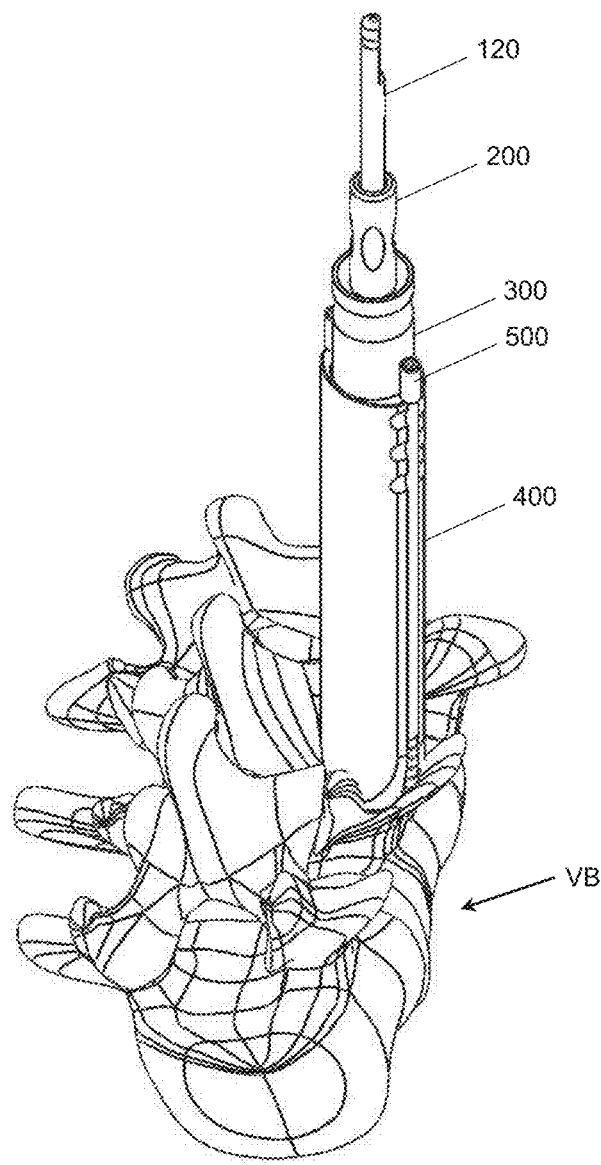
Figure 18:
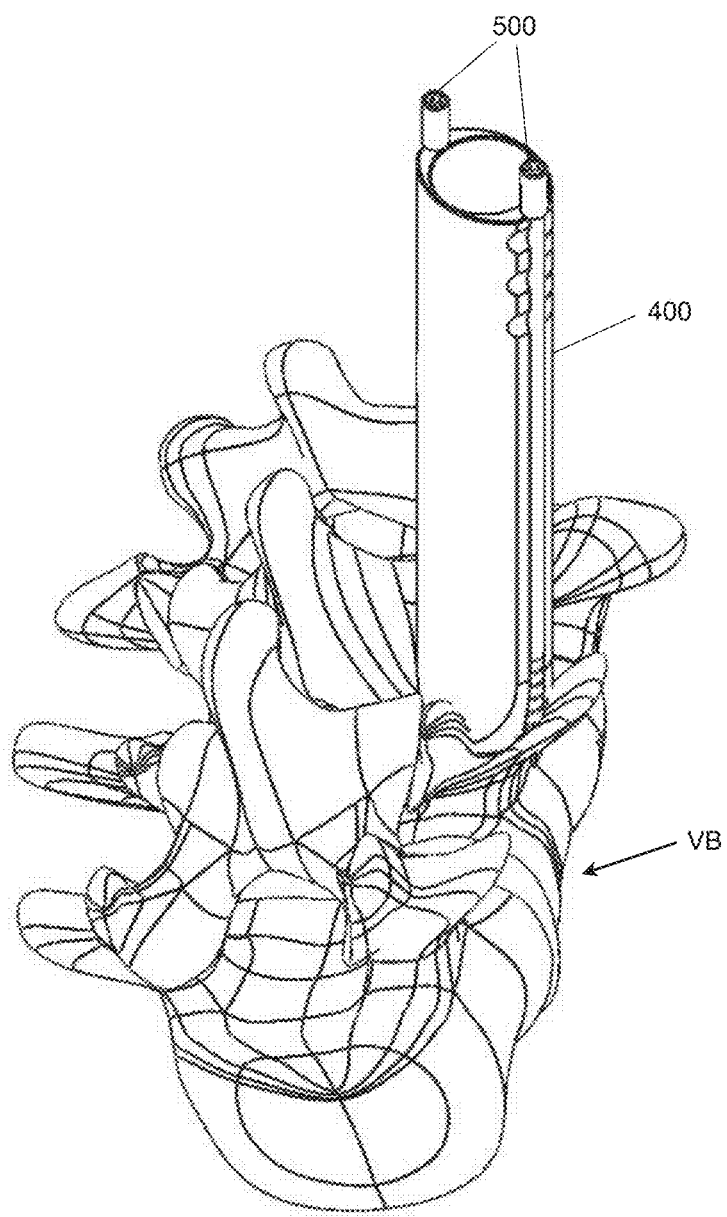

As illustrated in FIG. 16, the clinician next positions pin 500 over channel 402 of retractor tube 400. One or more pins 500 may be employed to secure refractor tube 400 to vertebral body "VB". In one embodiment, two pins 500 are employed. As illustrated in FIG. 17, the clinician may advance a first pin 500 into channel 402 and screw pin 500 into vertebral body "VB" such that head 502 is fully seated against the proximal end 401a of retractor tube 400 such that retractor tube 400 is securely fastened to vertebral body "VB". A second pin 500 may be secured in like fashion on an opposite side of retractor tube 400 as desired.

The clinician may next remove second dilator 300, first dilator 200, and elongate body 120 from longitudinal bore 405 of retractor tube 400 such that only retractor tube 400 remains. By removing all components from longitudinal bore 405, the clinician has clear access to vertebral body "VB" wherein the clinician may perform any further preparation, as needed.

Figure 19:
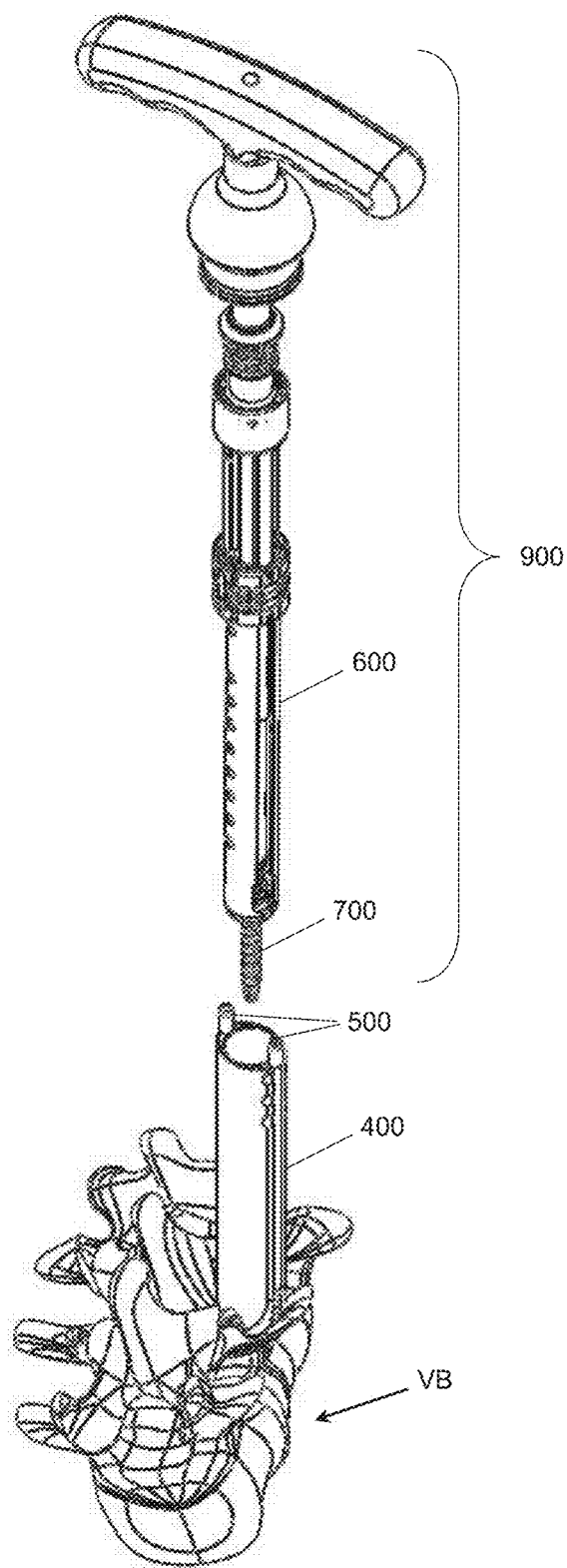

With elongate body 120, first dilator 200, and second dilator 300 removed from longitudinal bore 405 of retractor tube 400, the clinician may position a screw inserter 900 above retractor tube 400 as illustrated in FIG. 19. Screw inserter 900 includes a pedicle screw 700 and a retractor 600.

Figure 20:
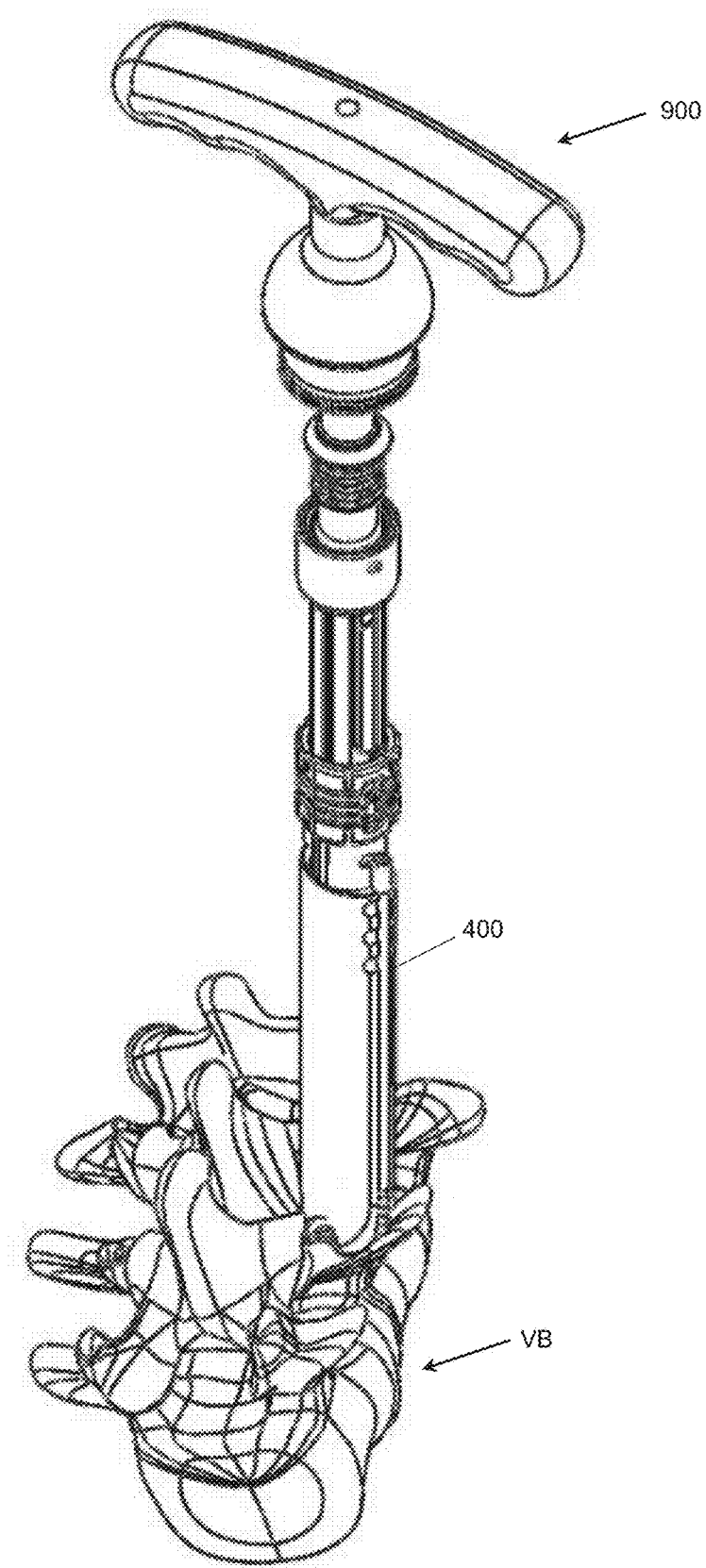

The clinician may advance screw inserter 900 within longitudinal bore 405 of retractor tube 400 as illustrated in FIG. 20. By advancing screw inserter 900 within longitudinal bore 405, pedicle screw 700 can be centered directly over the cannulated pedicle of vertebral body "VB".

Figure 21:
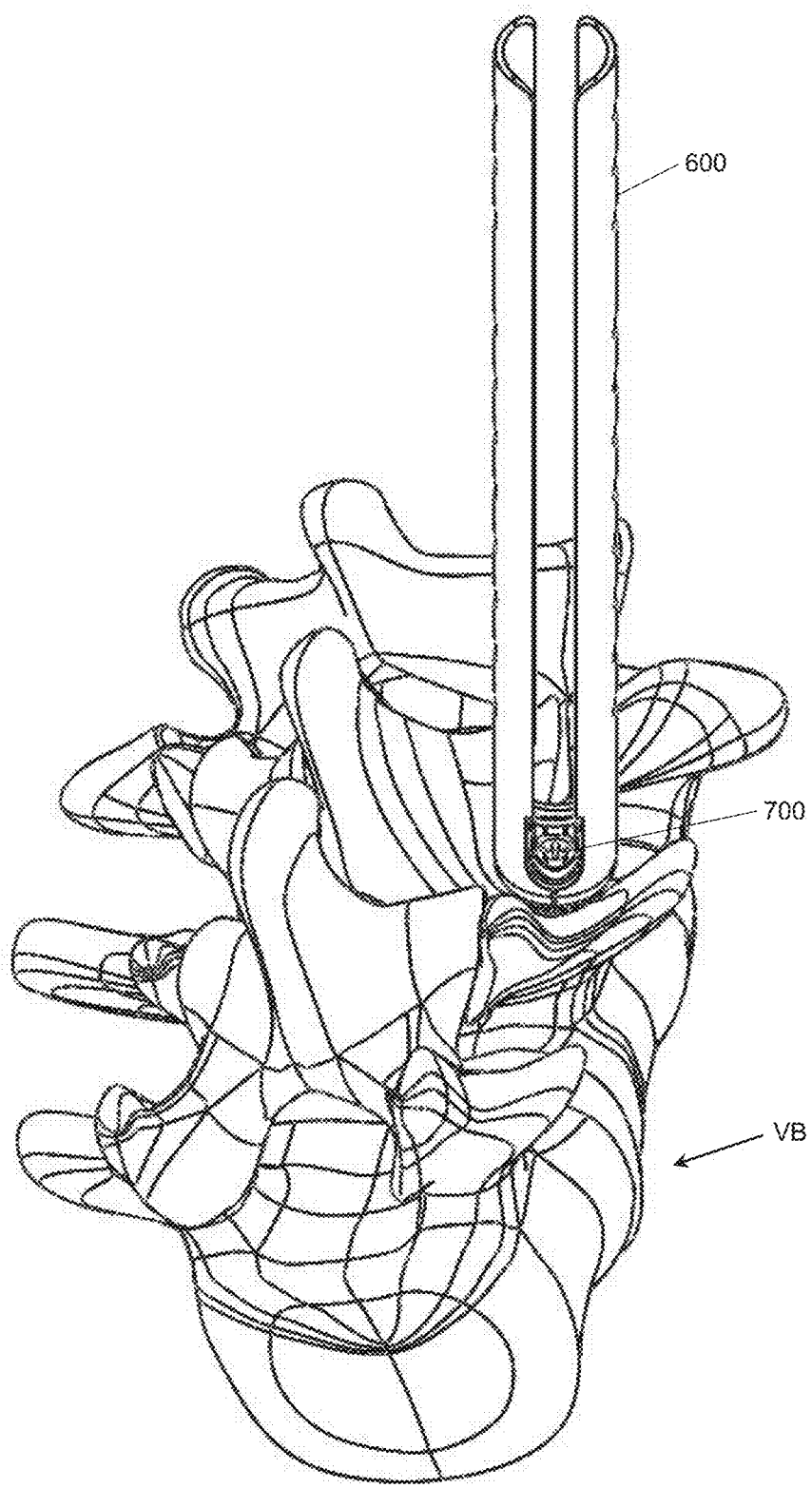

The clinician next configures screw inserter 900 to drive pedicle screw 700 in a direction that enables pedicle screw 700 to screw into the cannulated pedicle of vertebral body "VB" by rotating selection mechanism 913 to a first position. The clinician may rotate screw inserter 900 and securely fasten pedicle screw 700 and retractor 600 to vertebral body "VB". Next, the clinician may unthread screw inserter 900 from pedicle screw 700 and remove screw inserter 900 from longitudinal bore 405 of retractor tube 400. The clinician may unthread one or both pins 500 from vertebral body "VB" and remove retractor tube 400 and one or both pins 500 from the incision leaving retractor 600 and pedicle screw 700 securely fastened to vertebral body "VB" as illustrated in FIG. 21.

Any of the components of the presently disclosed devices can be formed of any suitable biocompatible material, including but not limited to, titanium, titanium alloys, stainless steel, cobalt chrome, and nickel titanium or polymer compositions.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A system for mounting a retractor tube comprising:
   an awl including an elongate body that extends between proximal and distal ends, the proximal end supporting a handle, the distal end having a bone engaging tip adapted to secure the awl to a vertebral body;

a first dilator having proximal and distal ends, the first dilator defining a longitudinal axis that extends between the proximal and distal ends of the first dilator, and a first longitudinal bore that extends through the first dilator, the first longitudinal bore adapted to receive the awl;

a retractor tube having a tubular body that extends between proximal and distal ends, the tubular body having an inner surface and an outer surface, the inner surface defining a second longitudinal bore that extends through the tubular body, the outer surface defining a plurality of channels; and a plurality of pins adapted to be received within the plurality of channels of the retractor tube to enable the plurality of pins to secure the retractor tube to a vertebral body, the plurality of pins configured to anchor in a vertebral body.

2. The system according to claim 1, wherein the first longitudinal bore has a diameter that is greater than a diameter of the elongate body of the awl.

3. The system according to claim 2, further including a second dilator, the second dilator defining a third longitudinal bore therethrough adapted for receiving the first dilator.

4. The system according to claim 3, wherein the second dilator has an outer surface that defines a spiral groove adapted to engage the inner surface of the retractor tube.

5. The system according to claim 1, wherein the awl has a removable handle.

6. The system according to claim 5, wherein the removable handle defines a fourth longitudinal bore configured to receive a portion of the elongate body of the awl.

7. The system according to claim 6, wherein the fourth longitudinal bore includes a D-shaped channel adapted to receive a D-shaped extension depending from the proximal end of the elongate body of the awl.

8. The system according to claim 1, wherein the distal end of the first dilator includes an outer surface that tapers in a distal direction along the longitudinal axis.

9. The system according to claim 1, wherein the distal end of the retractor tube is tapered.

10. The system according to claim 1, wherein each pin of the plurality of pins has a shank and a head, the shank configured to be received by at least one channel of the plurality of channels of the retractor tube.

11. The system according to claim 1, further including a screw inserter capable of supporting a retractor and a pedicle screw, the screw inserter being advanceable within the retractor tube and capable of securing the pedicle screw to a vertebral body.

12. The system according to claim 1, wherein the system is provided in the form of a kit.

13. A system for mounting a retractor tube comprising:
an awl including an elongate body that extends between proximal and distal ends, the proximal end supporting a handle, the distal end having a bone engaging tip adapted to secure the awl to bone;

a first dilator having proximal and distal ends, the first dilator defining a longitudinal axis that extends between the proximal and distal ends of the first dilator, and a first longitudinal bore that extends through the first dilator, the first longitudinal bore adapted to receive the awl;

a retractor tube having a tubular body that extends between proximal and distal ends, the tubular body having an inner surface and an outer surface, the inner surface defining a second longitudinal bore that extends through the tubular body, the outer surface defining a channel; and a pin adapted to be received within the channel of the retractor tube to enable the pin to secure the retractor tube to bone, the pin defining a shank extending between a head at aroximal portion thereof and a threaded distal portion configured to threadably engage bone.

* * * * *